United States Patent
Laub et al.

(10) Patent No.: US 6,190,608 B1
(45) Date of Patent: Feb. 20, 2001

(54) METHOD AND APPARATUS FOR INACTIVATING CONTAMINANTS IN BLOOD PRODUCTS

(75) Inventors: Ruth Laub, Brussels; Luc De Wael, Ranst; Mario Di Giambattista, Braine-le-Comte, all of (BE)

(73) Assignee: Croix-Rouge de Beligique Departement Central de Fractionnement, Brussels (BE)

(*) Notice: Under 35 U.S.C. 154(b), the term of this patent shall be extended for 0 days.

(21) Appl. No.: 08/983,294

(22) PCT Filed: Jul. 15, 1996

(86) PCT No.: PCT/BE96/00076

§ 371 Date: Mar. 23, 1998

§ 102(e) Date: Mar. 23, 1998

(87) PCT Pub. No.: WO97/03706

PCT Pub. Date: Feb. 6, 1997

(30) Foreign Application Priority Data

Jul. 14, 1995 (WO) .................................. PCT/BE95/00069

(51) Int. Cl.[7] .............................. A61K 41/00; C12N 7/04; C12N 13/00
(52) U.S. Cl. ........................ 422/24; 422/186; 422/186.3; 250/492.1; 250/455.11
(58) Field of Search ............................ 422/22, 24, 186, 422/186.3; 250/492.1, 432 R, 455.11

(56) References Cited

U.S. PATENT DOCUMENTS 5,024,766 * 6/1991 Mahmud .
5,133,932 * 7/1992 Gunn et al. .
5,834,420 * 11/1998 Laub et al. .

FOREIGN PATENT DOCUMENTS 0 018 561 4/1980 (EP) .
0 311 950 10/1988 (EP) .
07196531 * 8/1995 (JP) .

(List continued on next page.)

OTHER PUBLICATIONS

Photochemistry and Photobiology, 63(4): 541–546, *Protecting Fibrinogen with Rutin during UVC Irradiation for Viral Inactivation*, Gerard Marx, et al., (1996), (no month).

*Inactivation of Viruses during Ultraviolet Light Treatment of Human Intravenous Immunoglobulin and Albumin*, Hart el al., Vox Sang 1993; 64: 82–88 (1992), (no month).

(List continued on next page.)

*Primary Examiner*—Deborah Jones
*Assistant Examiner*—Jennifer McNeil
(74) *Attorney, Agent, or Firm*—Knobbe, Martens. Olson & Bear, LLP

(57) ABSTRACT

A method and apparatus for inactivating contaminants, particularly nonenveloped viruses, in blood products without the need for quenchers in the blood products. The blood product is flowed through a flow meter at a controlled flow rate and subjected to type C ultraviolet radiation, where the irradiation dose received by the blood product is less than 640 joules/m$^2$. The blood product does not contain quenchers when being irradiated, and the blood product retains more than 85% of its Factor VIII activity after being subjected to the radiation. The produced blood product is free of viruses and quenchers, avoiding potential toxicity due to the quenchers. The apparatus includes a source of UVC light, a quartz tube containing the blood product while it is exposed to the UVC light, a flow meter for controlling the flow rate of the blood product to be treated, and a pump. The UV light preferably emits light at 254 nm.

33 Claims, 5 Drawing Sheets

FOREIGN PATENT DOCUMENTS

| | | |
|---|---|---|
| 7-196531 * | 8/1995 | (JP) . |
| WO 94/03054 | 2/1994 | (WO) . |
| WO 94/28120 | 12/1994 | (WO) . |
| WO 95/00631 | 1/1995 | (WO) . |
| WO 96/02571 | 2/1996 | (WO) . |

OTHER PUBLICATIONS

*Virucidal Short Wavelength Ultraviolet Light Treatment of Plasma and Factor VIII Concentrate: Protection of Proteins by Antioxidants*, Chin et al., Blood, vol. 86, No. 11 (Dec. 1), 1995; pp. 4331–4336.

* cited by examiner

METHOD AND APPARATUS FOR INACTIVATING CONTAMINANTS IN BLOOD PRODUCTS

The present application is the U.S. national phase under 35 U.S.C. § 371 of International Application No. PCT/BE96/00076, filed Jul. 15, 1996.

OBJECT OF THE INVENTION

The present invention relates to a method for inactivating contaminants in blood products, especially whole blood, plasma, fluids comprising cellular blood compounds, and blood derivatives such as clotting factors (factor VIII, factor IX, von Willebrand's factor and the like), fibrinogen, fibronectin, immunoglobulins, albumin, and the like, including nonnatural products obtained by biological engineering, as well as the apparatus for carrying out the said method.

The present invention also relates to blood products treated by the method of the invention as well as pharmaceutical and/or cosmetic compositions comprising the said blood products.

TECHNOLOGICAL BACKGROUND OF THE INVENTION

The availability of blood products requires, for their use for therapeutic or nontherapeutic purposes, purification techniques which make it possible to obtain products of high purity, and preferably free of contaminants, in particular of viral contaminants.

In blood products, the viral contaminants may be enveloped viruses (HIV, hepatitis B, C, D, E and G viruses, and the like) or nonenveloped viruses (hepatitis A virus, parvovirus, and the like).

For many years, various international or national bodies have introduced increasingly strict standards for the preparation of blood products so as to prevent their application for therapeutic or nontherapeutic purposes when they contain viral contaminants (Council Directives 65/65 EEC, 75/319/EEC & 89/381 EEC).

At the European level, the CPMP standards (CPMP/BWT 268/95 and 269/95) require the use of certain treatments against enveloped or nonenveloped viruses.

It is in particular mentioned in these documents that an inactivation step using heat (dry or steam) or using pasteurization in the preparation of clotting factors is effective against the hepatitis A virus, but would not be very effective against other nonenveloped viruses, in particular parvoviruses.

On the other hand, a treatment comprising a chemical inactivation step (by addition of solvents-detergents) is effective for enveloped viruses but ineffective for treating nonenveloped viruses.

It is also known to use certain chemical agents such as beta-propiolactone, which is effective in the treatment of nonenveloped viruses but has the disadvantage of modifying the treated proteins.

It is also known that certain long treatments using pH modification, below pH 4, or the addition of proteases allows activation of some nonenveloped viruses such as parvoviruses. However, these treatments also modify the conformation and structure of the treated proteins.

Consequently, it is known that, to date, the majority of the physicochemical treatment steps capable of being used to obtain viral inactivation of blood products are either highly toxic, or unacceptably affect the conformation of the treated proteins, or are ineffective for treating nonenveloped viruses, in particular parvoviruses.

Parvoviruses are small nonenveloped DNA viruses which infect numerous animal species, including man (Handbook of Parvoviruses, Vol. 1, pp. 1–30, Disinfection, Sterilization and Preservation, Fourth Edition, Seymour S. Block, Ed. Lea & Febiger, Philadelphia-London). They are endemic in nature and cause a wide variety of diseases whose appearance largely depends on the state of development of the host.

Among these, parvovirus B19 is the only known member of the Parvoviridae family which is pathogenic for man. Likewise, murin parvovirus Hi can also infect man.

Parvovirus B19 infection in a healthy man may be asymptomatic or may induce benign diseases (example: fifth disease in children).

On the other hand, in immunodeficient patients or patients suffering from blood disorders, it may lead to chronic anaemias and to transient aplasias which may be associated with haemolytic anaemias.

Passing through the placenta, it may cause intrauterine death. It exhibits a remarkable tropism for the erythroid lines of human haematopoietic progenitor cells.

A recent epidemiological survey has shown that 50 to 60% of the adult French population and 36% of 1- to 15-year-old children have a positive parvovirus serology.

The process of viral DNA has been demonstrated by genetic amplification (PCR) in a number of batches of purified factor VIII concentrates, regardless of the methods of viral inactivation used.

This has been confirmed by the $B19^+$ serology detection, without clinical sign, in 85% of haemophilic children who have received, since birth, only highly purified factor VIII concentrate (FVIII THPSD) used in France since 1988, free of any contamination with enveloped viruses (HIV, HBV, HCV) (Y. Lauriau et al., 1er congrès de la Société Francaise de Transfusion [1st conference of the French Transfusion Company] (1994)).

This observation indeed demonstrates that, without new methods of viral inactivation, targeted at the selective elimination of parvoviruses, in particular of parvovirus B19, from blood products, the probability of contamination is high.

Parvoviruses are extremely resistant, even at high temperature. Their haemagglutination properties and their infectivity are not affected by chemical treatments, such as chloroform or various acids, and most resist enzymatic digestions using RNase, DNase, papain or trypsin.

STATE OF THE ART

International Patent Application WO95/00631 describes a method of viral inactivation of blood products comprising the addition to these blood products of products which are photoactivable by UVA radiation and which would become toxic for the viruses present in these blood products. This method comprises a step which makes it possible to isolate these toxic reagents from the blood products so that the latter are not contaminated with these toxic agents.

Among these toxic agents, psoralen may be mentioned in particular.

However, this method has the disadvantage that it cannot be guaranteed that the treated blood products will not be completely free of these photoactivable agents which would be capable of denaturing and/or inactivating the treated blood products and causing toxicity in man or animals when they are reinjected repeatedly, even at a low dose, with the treated blood products.

It is also known that it is possible to sterilize a large number of products by subjecting them to ultraviolet radiation. It is in particular known from the document "Sterilization by Ultraviolet Irradiation" (chapter 31, I L SHECHMEISTER) that ultraviolet radiation is capable of destroying contaminants such as viruses, mycoplasmas, bacteria and fungi. Such a radiation may be used in particular in media such as gases or liquids.

It is also known from the document by Chin S. et al. (Blood, volume 86, No. 11, December 1995, p. 4331–4336) to treat blood products with type C ultraviolet radiation in the presence or in the absence of antioxidants such as rutin and to obtain the inactivation of nonenveloped viruses, particularly parvoviruses.

In addition, the methods of viral inactivation of the state of the art can affect the integrity and the activity of blood products (in particular the three-dimensional conformation of clotting factors such as factor VIII) and consequently their activities.

Furthermore, the methods of viral inactivation of the state of the art often exhibit difficulties in relation to their validation, because they exhibit problems of reproducibility or of monitoring. Indeed, certain treatment parameters must be modified or cannot be easily maintained, in particular when the degree of humidity has to be monitored if a treatment is carried out with dry heat. Furthermore, it is difficult to control the various steps of the operating procedures.

AIMS OF THE INVENTION

The present invention aims to obtain a new method and an apparatus for inactivating contaminants present in blood products, which do not exhibit the disadvantages of the state of the art and which are simple, rapid, inexpensive and reproducible.

Another aim of the present invention is to develop a method of viral inactivation which preserves the integrity of blood products, in particular that of clotting factors such as factor VIII, factor IX, von Willebrand's factor, fibronectin, fibrinogen and the like.

A further aim of the present invention is to obtain a method and an apparatus which can be easily validated and which are in accordance with good pharmaceutical manufacturing practices (GMP) and with European standards (CPMP).

A last aim of the present invention is to obtain a method and an apparatus for viral inactivation of blood products which make it possible to inactivate nonenveloped, preferably single-stranded, viruses such as parvoviruses, in particular parvoviruses B19 and H1. The present invention also aims to obtain the said blood products free of the said contaminants, in particular of nonenveloped viruses such as parvoviruses, in particular parvoviruses B19 and H1, without the activity of the blood product being affected.

CHARACTERISTICS FEATURES OF THE INVENTION

The present invention relates to a new method of inactivating parvoviruses, in particular parvoviruses B19 and H1, present in a blood product, according to which the said blood product is subjected to one or more emission(s) of type C ultraviolet radiation.

"Blood product" is understood to mean any blood product, liquid or solid, obtained naturally from the human or animal body or by the synthesis route such as whole blood, its cellular compounds, its derivatives such as serum or plasma and blood protein compounds, namely clotting factors (factor VIII, factor IX, von Willebrand's factor and the like), fibrinogen, fibronectin, immunoglobulins, albumin and the like, including protein compounds obtained by biological engineering, such as recombinant proteins or synthetic peptides.

These products may also be factors produced by certain specific blood cell lines such as interferons, interleukins, or cell receptors for these molecules obtained naturally or by the synthetic route, particularly the recombinant peptides or proteins obtained by the recombinant DNA technique. Advantageously, this method also causes inactivation of other contaminating agents such as nonenveloped viruses (HAV), enveloped viruses (HIV, hepatitis B, C, D, E and G viruses and the like), bacterial agents and the like, which may be present in the blood product.

The method according to the invention may also be combined with one or more additional treatment(s) for inactivation of contaminants, particularly viral contaminants, well known to persons skilled in the art, in particular physical or chemical viral inactivation treatments chosen from the group consisting of one or more dry or wet heating step(s), the addition of chemical components, in particular of solvent-detergent or products which become active under ultraviolet radiation, one or more pasteurization step(s), subjection to one or more emissions of particular radiation such as $\gamma$ radiation or X-rays or a combination of these methods. Among the active products capable of being added to blood products, there may be mentioned in particular agents which protect against free radicals (vitamin C and the like) and betapropiolactone which causes a phenomenon of alkylation of proteins. Such products should be used at doses which do not cause a toxicity phenomenon or denaturation of the treated blood products. However, at the irradiation doses used according to the invention, the addition of such products is not necessary in order to cause inactivation of nonenveloped viruses or to ensure protection against free radicals.

The method of viral inactivation of the invention may be combined with a general method of isolating or separating blood derivatives from whole blood.

This method may comprise one or more filtration, precipitation or chromatographic separation step(s) and the like which make it possible to separate the various components of whole blood from each other.

According to the invention, most of the emission of UVC radiation occurs between 250 and 270 nm, preferably at the wavelength of 254 nm, that is to say the preferred region of absorption of nucleic acids and the irradiation doses received by the products are between 10 and 2000 joules/m$^2$, preferably between 230 and 400 joules/m$^2$.

In the method according to the invention, the irradiation doses and the wavelength used are chosen so that the irradiation doses received by the treated blood product affect essentially the nucleic acids of the contaminants, without disrupting the structure of the peptides or the proteins present in the treated blood product.

Unexpectedly, the Inventors have observed that it was possible to treat blood products in thin layers ("monolayers" or so-called laminar layers) or otherwise, that is to say that there are no limiting factors for the volumes treated. This property is particularly advantageous because by treating blood products which are not in thin layers, it is possible to avoid the disruption phenomena which exist at the solid/liquid surface when the work is carried out in thin layers. In addition, by not working in thin layers, it is possible to treat large quantities of blood products and to avoid problems of heating and shearing of the treated products (BAILEY, Bioch. Fond, McGraw-Hill).

The wavelength of emission of UVC radiation and the irradiation doses can be adjusted by persons skilled in the art according to the quantity and type of blood products to be treated. It should be noted that the higher the irradiation doses received by the blood product to be treated, the better the inactivation of the contaminants present. However, in order to reduce the phenomenon of denaturation of the blood product, persons skilled in the art will adjust the irradiation dose of the UVC emission wavelength so as to reduce the denaturation and the loss of activity of the said blood products. This adjustment will be made so as to be in accordance with the European CPMP standards (CPMP/BWP268/95 and 269/95).

It is possible to obtain complete viral inactivation of the parvoviruses present (that is to say that it is no longer possible to identify viruses above the detection threshold) while limiting the irradiation doses received and allowing a reduction in loss of activity of the said product of less than 10–150, preferably less than 5%.

The present invention also relates to a device for inactivating parvoviruses, in particular parvoviruses B19 and H1, present in a blood product allowing the advantageous use of the method of the invention.

This device essentially relates to an emitter of type C ultraviolet rays, that is to say an emitter of rays whose wavelength is advantageously between 230 and 270 nm, preferably at a wavelength of the order of 254 nm, which is the maximum region of absorption of ultraviolet rays by nucleic acids of the viruses treated. In this device, the radiation is directed towards the blood product to be treated.

This device allows irradiation doses of between 10 and 2000 joules/m$^2$ received by the blood product to be treated, preferably irradiation doses of the order of 230 to 400 joules m$^2$ received by the blood product to be treated.

The present invention also relates to the apparatus comprising the inactivation device according to the invention.

This apparatus also comprises devices which ensure the isolation or the separation of blood derivatives from whole blood.

These devices may comprise means of precipitation, centrifugation/decantation, filtration, concentration or dialysis of the blood product to be treated which can be adjusted by persons skilled in the art according to the blood products separated and treated.

Preferably, the blood product brought into contact with the ultraviolet C radiation is placed in a quartz tube or a tube made of a polymerized material which generally does not absorb in the region of wavelength emitted by-the ultraviolet C radiation. The apparatus may also comprise a device allowing the addition, to the blood product, of an agent which protects against free radicals capable of being generated by the ultraviolet radiation. Such agents may consist of vitamins such as sodium ascorbate, glutathione, or other products (SOD) well known to persons skilled in the art. In addition, the apparatus may also comprise a device allowing the addition, to the blood product, of various chemical compounds capable of inactivating certain contaminants present in the blood products to be treated. These compounds may be in particular products which become active under ultraviolet radiation and which are capable of being combined with the method of the invention so as to obtain a synergistic effect on other contaminants present in the said blood product. However, it is important to note that, contrary to techniques using nonpenetrating UV radiation which apply in particular to blood products provided in thin layers, it is possible, according to the invention, to treat a blood product without resorting to the application of thin layers and without addition of toxic additives for viral inactivation.

The present invention also relates to the blood product obtained by the method of the invention free of viral contaminants, in particular free of nonenveloped single-stranded or double-stranded DNA or RNA viruses, particularly parvoviruses such as parvoviruses B19 and/or H1, the said blood product, in particular the blood derivative such as a clotting factor, being characterized by the retention of more than 85%, preferably more than 95%, of its activity. The measurement of loss of efficacy is carried out according to procedures known to persons skilled in the art.

The present invention will be described in greater detail in the following nonlimiting examples with reference to the accompanying figures.

DESCRIPTION OF A PREFERRED EMBODIMENT OF THE INVENTION

Figure 1:
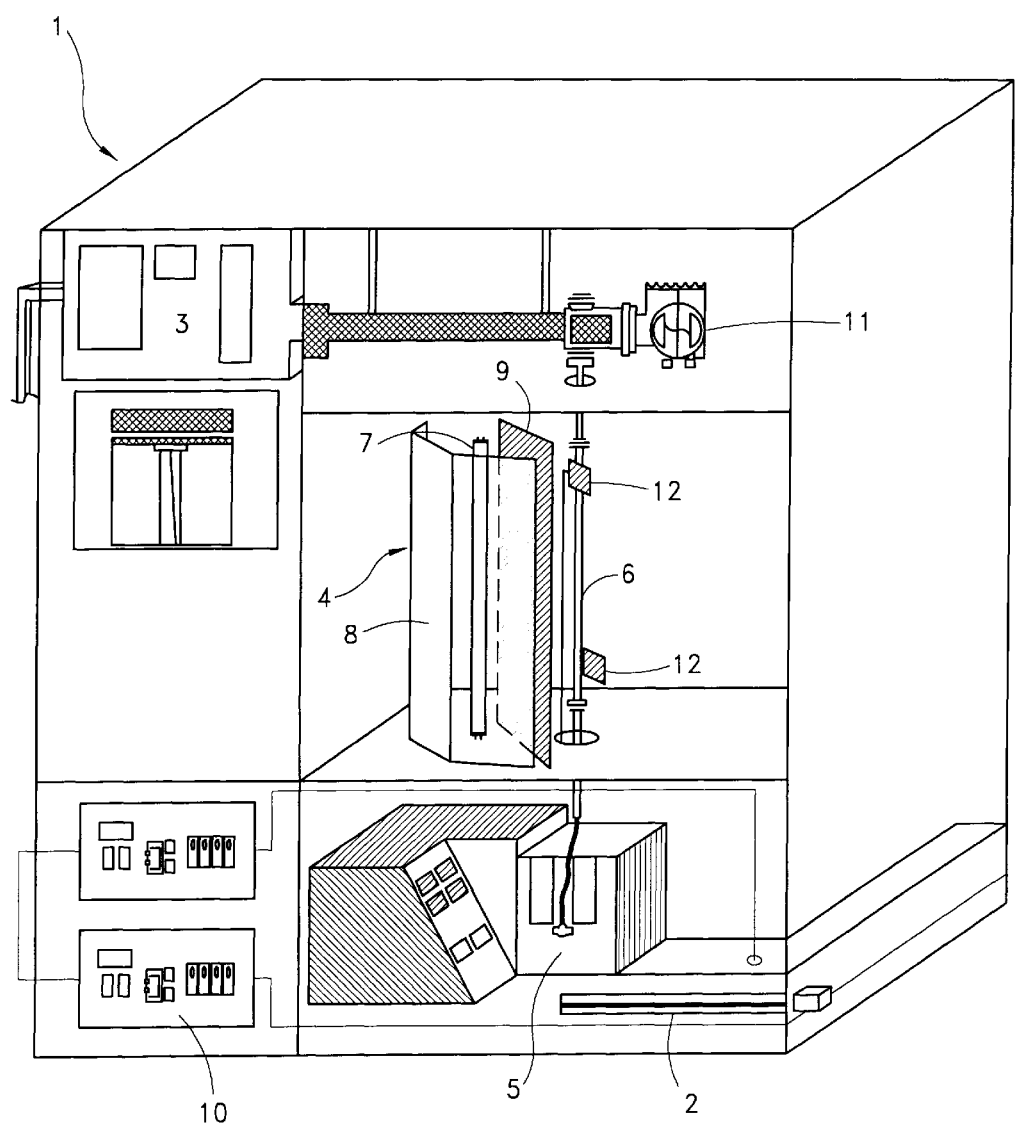
FIGS. 1 and 2 represent schematic examples of apparatus according to the present invention.
Figure 2:
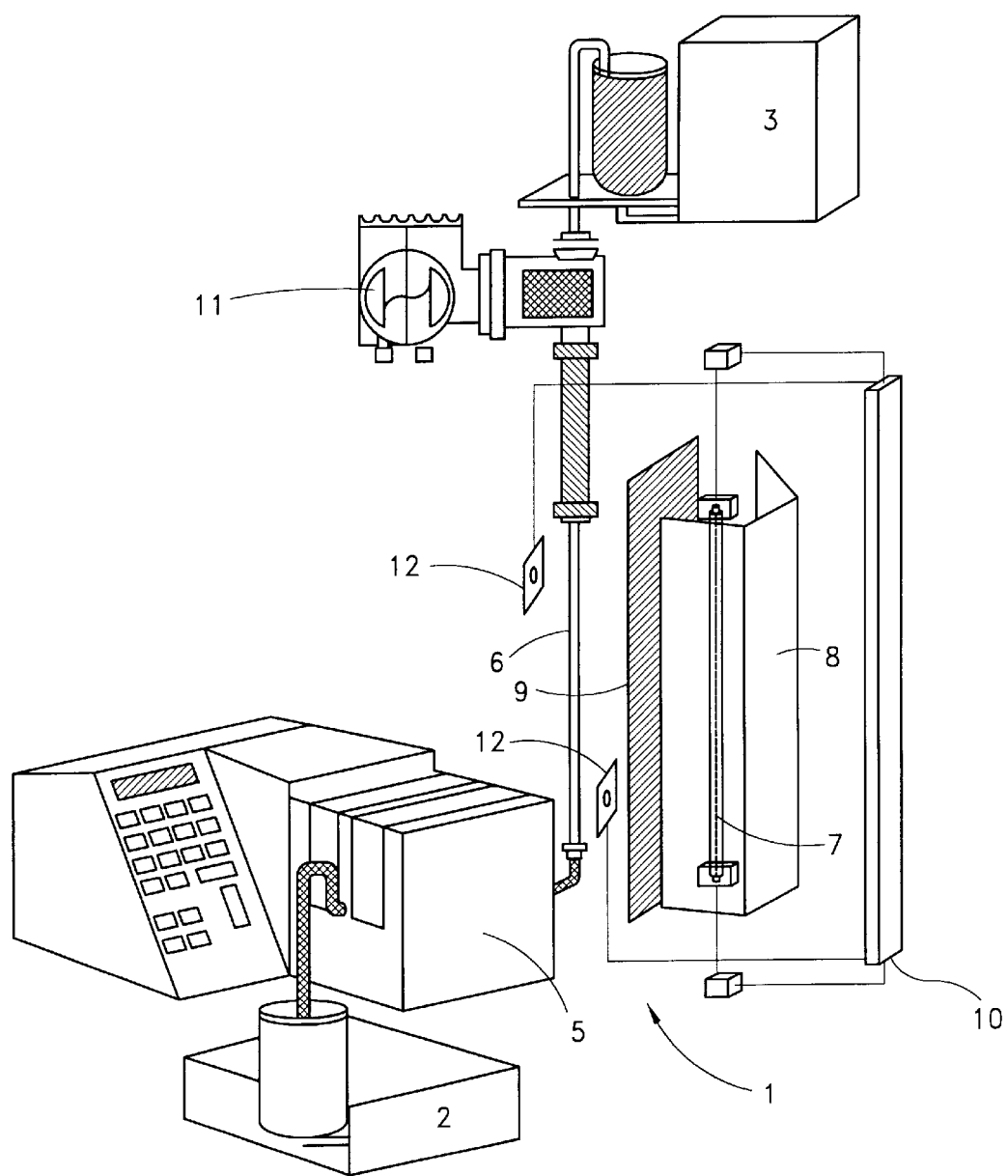
Figure 3:
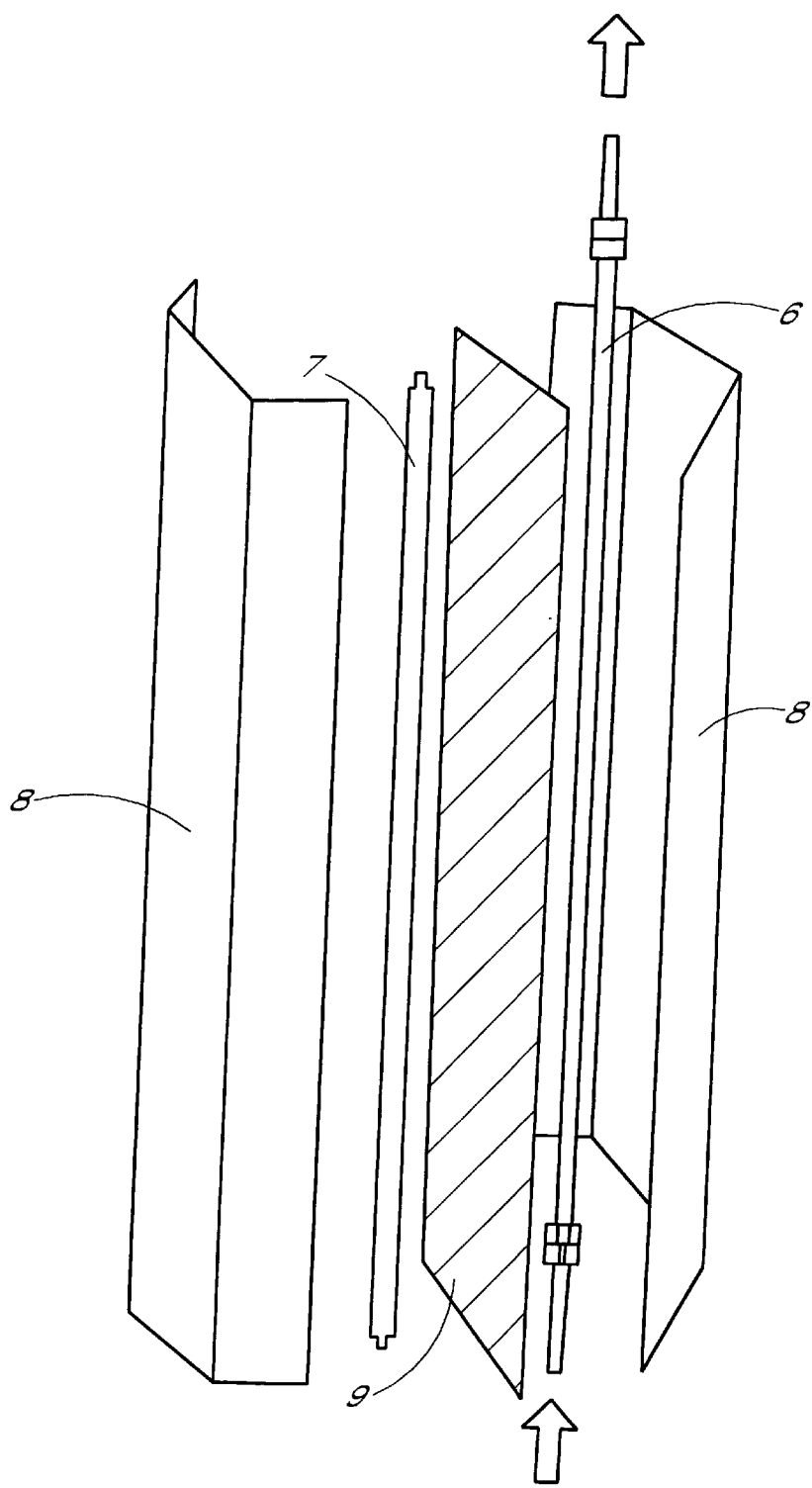
FIG. 3 represents a schematic detail of the apparatus according to the present invention.

In FIGS. 1 to 3, an apparatus for the preparation of a blood product according to the invention is represented.

This apparatus 1 comprises devices (2, 3) which bring about in particular precipitation, centrifugation/decantation, filtration, concentration and dialysis of blood products such as factor VIII or fibrinogen, and which can be adapted by persons skilled in the art according to another blood product treated.

This apparatus also comprises the device 4 according to the invention which brings about, by a physical treatment, viral inactivation of the said blood product.

The blood product according to the invention is brought by a pump in a quartz tube 6 to the device 4.

This device comprises a UV lamp 7, preferably of disinfection UV tube type, in which more than 90% of the emission occurs between 230 and 270 nm, preferably at a wavelength of the order of 254 nm, this lamp being mounted in a reflecting chamber 8, cylindrical or otherwise, which sends the radiation towards the quartz tube 6 placed at the focus of the reflecting chamber 8.

In the device of the invention, no contact is possible between the product circulating in the quartz tube 6 and the UV lamp 7.

A system for turbulence, such as a baffle or an injection of nitrogen, makes it possible to maintain a homogeneous flow in the quartz tube 6.

The apparatus also comprises a pump 5 and a flow meter 11 which makes it possible to control the flow rate of the blood product to be treated and to vary the passage time of the blood product in front of the UV lamp 7.

In addition, the device may comprise one or more screens 9 placed between the quartz tube 6 and the UV lamp 7. The appropriate choice of screens makes it possible to vary the irradiation doses received by the blood product to be treated and the specific choices of emitted wavelengths. It is also possible to vary the irradiation doses received by the blood product to be treated by adjusting the choice of the UV lamp used (it being possible to use different lamp powers), by selecting the screens used and by adjusting the flow rate of the blood product passing in front of the lamp. These modifications can be adjusted by persons skilled in the art according to the quantity and type of blood product treated. Furthermore, a system 10 for controlling the quantity of ultraviolet C which irradiates the quartz tube 6 (and therefore the irradiation dose received by the blood product) is placed on the opposite side relative to the UV lamp 7.

This control system comprises, as represented in the figures, one or more sensor(s) 12 advantageously placed on either side of the quartz tube 6 and optionally on either side of the screen 9, so as to enable persons skilled in the art to adjust the rate of flow of the blood product according to the type of blood product to be treated and according to the irradiation doses emitted by the UV lamp 7.

The residence time of the blood product may be adjusted in order to obtain a constant dose of irradiation. The diameter of the tube may be adjusted to the volume to be treated as well as the power or the length of the disinfection lamp. The temperature is controlled and recorded both inside the device and in the fluid (blood product).

The apparatus and the device according to the invention may also comprise means for controlling the temperature of the blood products, which may consist of cooling means such as a refrigerating device or a fan.

The various materials used in the device and the apparatus according to the invention are advantageously essentially disposable products such as stainless steel 316L, Teflon, and the like, which are in agreement with good pharmaceutical manufacturing practice (GMP) and which can be hygienically treated on site.

The device for viral inactivation by ultraviolet C radiation is advantageously placed downstream of the general method for treating and separating a blood product, for example before sterilizing filtration or after ultrafiltration of the blood product. The simplicity and the small size of the portable device of the invention advantageously allows its use for the inactivation of any type of blood product without considerably modifying an apparatus for the preparation, purification or separation of blood products.

The device and the apparatus according to the invention can be constructed in a single block or as juxtaposed portable modules placed in series or in parallel. The irradiation doses received by the blood product treated are particularly low and vary between 10 and 2000 joules/m$^2$ and are preferably of the order of 230 to 400 joules/m$^2$. Unexpectedly, these irradiation doses are sufficient to obtain the desired viral inactivation.

The power of the ultraviolet lamp is advantageously preferably between 4 and 132 Watt, preferably between 8 and 60 Watt, so as to preserve the integrity of the products treated. It should be noted that, using the method of the invention, the activity of the blood product (in particular of clotting factors, fibrinogen or immunoglobulins) is not greatly affected (on average less than 5% reduction in activity).

The UV lamp used in the apparatus according to the invention is preferably of SPA® type, in particular that produced by the company AQUAFIN VALENCIA (California, USA).

In the following examples, various measurements of viral inactivation which are obtained on samples of blood products infected with parvoviruses and other nonenveloped viruses are given.

EXAMPLE

1. Materials and Methods

Because of the problems caused by the use of certain human parvoviruses and the problems of culturing these parvoviruses, in particular parvovirus B19, in vitro, the murin parvovirus $MVM_p$, which has a very similar size and shape, is used as model for developing methods allowing the inactivation of parvovirus B19. The murin parvovirus MVMp was chosen because this type of parvovirus is less sensitive than parvovirus B19 to inactivation by ultraviolet radiation or by temperature modification.

The tests are compared to the inactivation of a nonenveloped RNA virus.

EMC (encephalomyocarditis) is a member of the Picornaviridae family, whose inactivation has been studied as model of nonenveloped RNA virus. The EMC virus is a murin virus which can be used as model of contamination with the hepatitis A virus in man. $10^6$ pfu/ml for EMC and $10^{10}$ pfu/ml for MVMp are inoculated into various samples of blood product (cryoprecipitate, factor VIII or immunoglobulins).

2. Measurement of Active Virus Titre

The virus reduction index was determined according to the recommendations of the European Communities (EEC Regulatory Document not for guidance, Biologicals 1991, 19, p. 251) and expressed as logarithmic reduction. The measurements of titre can be carried out according to the methods described by Tattersall P. (J. Virol., 10, pp. 586–590 (1972)) and by Russell S. J. et al. (J. Virol., 66, pp. 2821–2828 (1992)).

The cell lines chosen to be infected with the parvoviruses are the NB324/k human cell line (described by Tattersall et al.) and the L929 line (clone 929 of the A9 ATCC, CCL 1.4 line).

The titration is carried out by in situ hybridization of the infectious centres (replicative centres) with the use of a radioactively labelled probe. The detection is carried out on nitrocellulose filters. The determination of the virus titre can be carried out by lysis plaque or by limiting dilution method ($TCID_{50}$-Sperman-Kärber method).

The blood products treated by the method of the invention are a cryoprecipitate of plasma, factor VIII, previously treated or otherwise by addition of solvent/detergent, fibrinogen and immunoglobulins.

3. Results

The method (each step) and the apparatus of the invention comply with the requirements of the validations required by the European authorities (CPMP/BWP/268/95 and CPMP/BWP/269/95 respectively operational from Aug. 14 and Sep. 13, 1996 (incorporated herein by reference)). In accordance with the recommendations of these authorities (§ 5.2.1 (1) CPMP/BWP/269/95), the method and the apparatus of the invention comprise at least one operating step of effective treatment against nonenveloped viruses, in particular parvovirus B19 (§ 5.2.2 (iii)). The invention meets in particular the requisite inactivation requirements, namely 5 to 9 log reduction (cf. Annex I CPMP/BWP/268/95), that is to say that it is possible to eliminate all the inoculated viruses.

Indeed, the Inventors did not observe, after treatment, any virus multiplication above the detection threshold.

Figure 4:
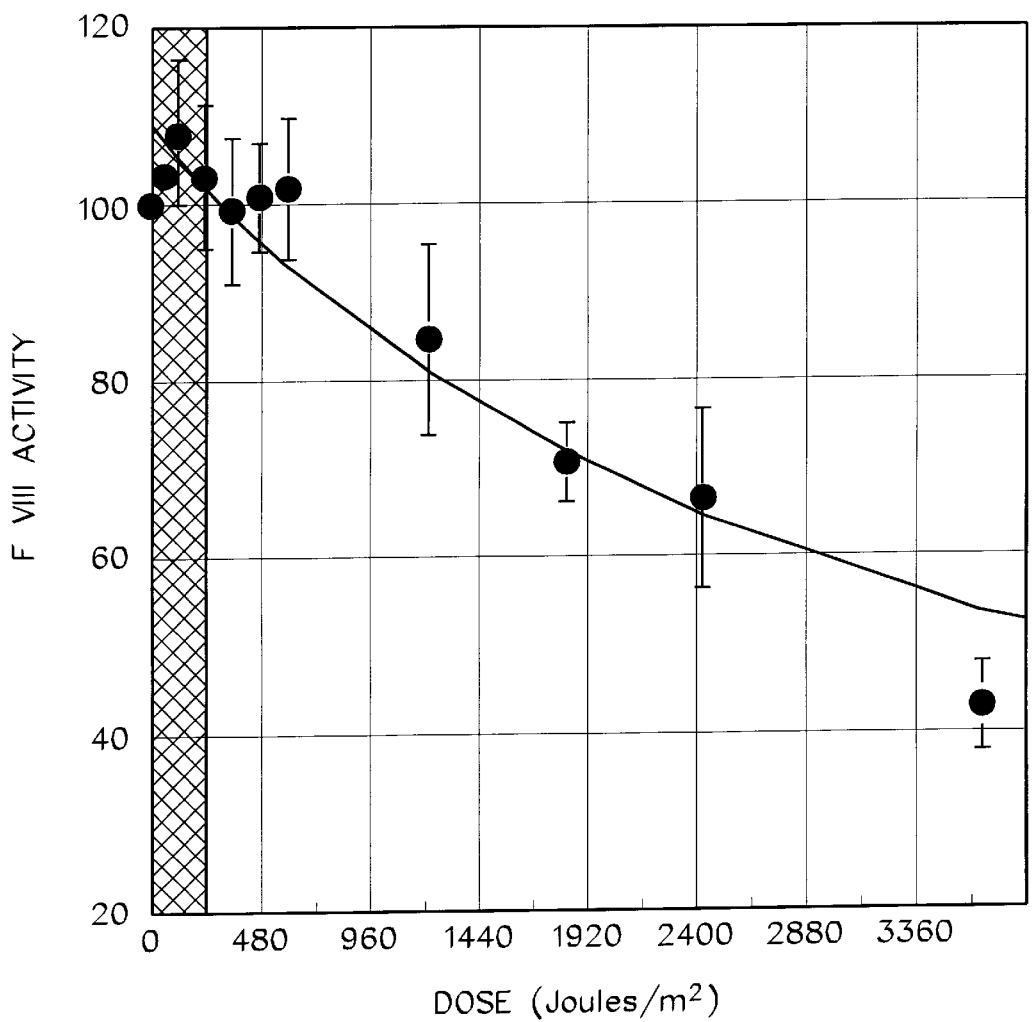
FIG. 4 represents the percentage of preserved factor VIII activity measured in chromogenic medium as a function of increasing irradiation doses of ultraviolet rays received by factor VIII.
Figure 5:
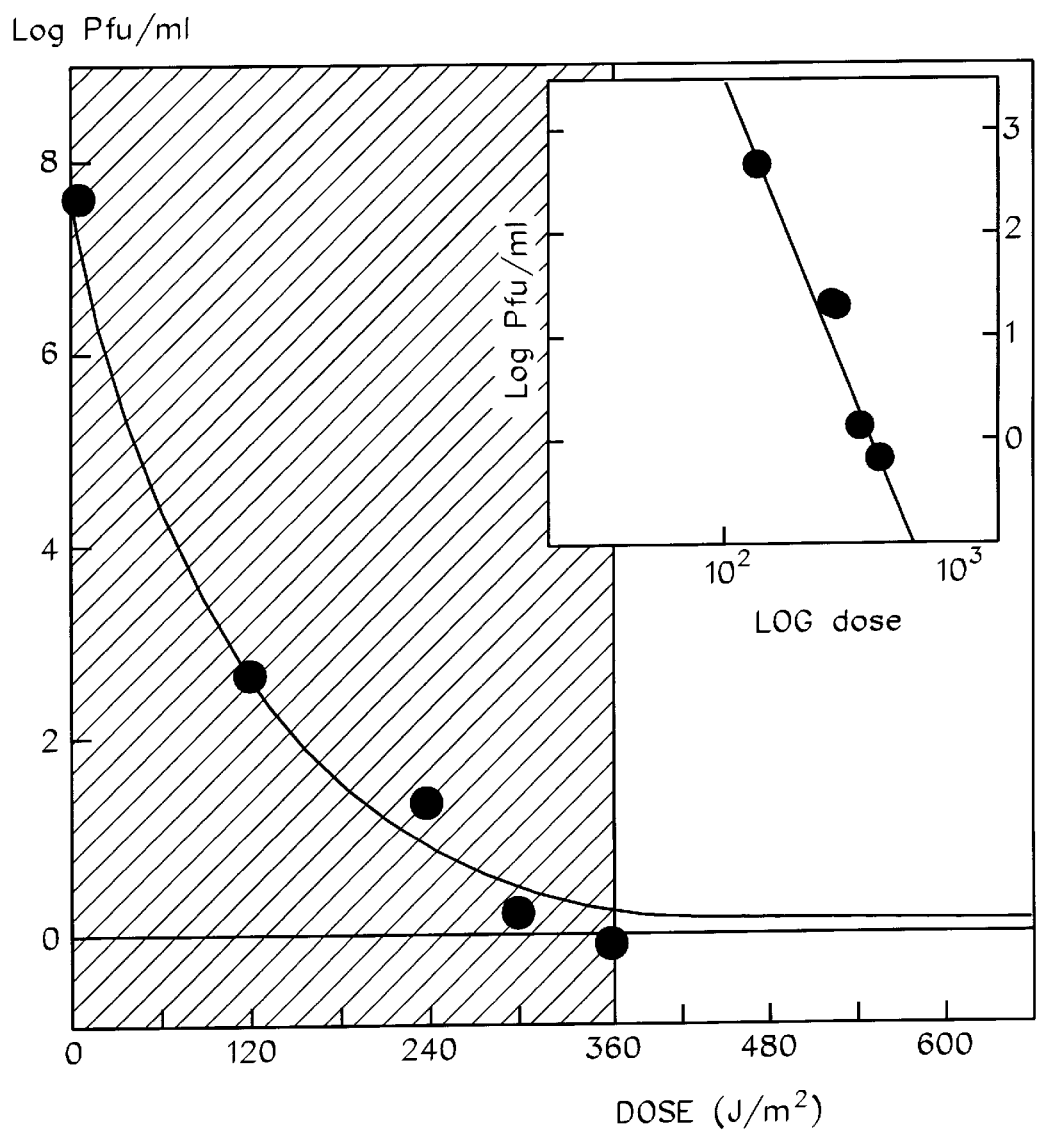
FIG. 5 represents the titration of the parvovirus MVMp inoculated into a solution of factor VIII treated at increasing irradiation doses of ultraviolet rays, the irradiation doses being the doses received. This measurement is also represented by giving the logarithmic values.

As indicated in FIG. 4, increasing doses of ultraviolet radiation cause inactivation of blood derivatives such as factor VIII. However, the Inventors unexpectedly observed that it is possible to obtain inactivation of parvoviruses by irradiation, by means of ultraviolet C radiation, of the viruses inoculated into solutions comprising factor VIII, while limiting the irradiation doses, without substantially affecting the activity of the blood derivatives (see FIG. 5).

In Table 1 below, a logarithmic reduction ($\log_{10}$) of the viruses inoculated into a composition comprising immunoglobulins is observed. These logarithmic reduction values are given for increasing doses of irradiation by ultraviolet C radiation which are received by the said immunoglobulins.

TABLE 1

| | Logarithmic reduction ($\log_{10}$) | | | | | |
|---|---|---|---|---|---|---|
| | Dose (joules/m$^2$) | | | | | |
| Type of virus | 60 | 120 | 180 | 240 | 600 | 1000 |
| MVMp | 3.08 | 4.73 | 5.60 | 6.33 | n.d. | n.d. |
| EMC | 1.53 | 3.04 | 3.84 | 4.49 | 5.07 | n.d. |

The concentration of immunoglobulins in the solution is 2 mg/ml.

Similar results are obtained with the other blood products treated.

What is claimed is:

1. A method of inactivating nonenveloped viruses present in a blood product, comprising flowing the blood product past one or more emission(s) of type C ultraviolet radiation while controlling the flow of the blood product such that the irradiation doses of ultraviolet radiation which are received by the blood product are lower than 640 joules/m$^2$ and the blood product retains more than 85% of its activity and is substantially free of nonenveloped viruses, wherein the blood product does not contain quenchers when said blood product is subjected to said one or more emissions of type C ultraviolet radiation.

2. A method according to claim 1, wherein the irradiation doses of ultraviolet irradiation which are received by the blood product are between 10 and 400 joules/m$^2$.

3. A method according to claim 2, wherein the irradiation doses of ultraviolet radiation which are received by the blood product are between 200 and 400 joules/m$^2$.

4. A method according to claim 1, wherein the blood product is selected from the group consisting of whole blood and a cellular compound.

5. A method according to claim 4, wherein the blood product is selected from the group consisting of platelets and erythrocytes.

6. A method according to claim 1, wherein the blood product is selected from the group consisting of serum, plasma and blood protein compounds.

7. A method according to claim 6, wherein the blood protein compounds are selected from the group consisting of clotting factors, factor VIII, factor IX, von Willebrand's factor, fibrinogen, fibronectin and a mixture thereof.

8. A method according to claim 6, wherein the blood protein compounds are selected from the group consisting of immunoglobulins, albumin and a mixture thereof.

9. A method according to claim 1, wherein most of the emission of type C ultraviolet radiation occurs between 250 and 270 nm.

10. A method according to claim 1, wherein most of the emission of type C ultraviolet radiation occurs at a wavelength around 254 nm.

11. A method according to claim 1, wherein the method is combined with one or more other physical or chemical viral inactivation treatments.

12. A method according to claim 11, wherein the other methods of viral inactivation are a physical or chemical viral inactivation treatment method selected from the group consisting of one or more (dry or wet) heating step(s), the addition of chemical components, one or more pasteurization step(s), subjection to one or more emission(s) of particular radiations and a combination of these methods.

13. A method according to claim 12, wherein the other methods of viral inactivation are selected from the group consisting of γ-radiation and X-rays.

14. A method according to claim 1, wherein the method is combined with a general method of isolating or separating blood derivatives from whole blood.

15. A method of viral inactivation according to claim 1, wherein the blood product is not treated in thin layers.

16. A blood product obtained by the process according claim 1.

17. A blood product according to claim 16, wherein the blood protein compounds have retained more than 95% of their activity.

18. A blood product according to claim 16, wherein the blood product is selected from the group consisting of serum, plasma and blood protein compounds.

19. A blood product according to claim 18, wherein the blood protein compounds are selected from the group consisting of clotting factors, factor VIII, factor IX, von Willebrand's factor, fibrinogen, fibronectin and a mixture thereof.

20. A blood product according to claim 18, wherein the blood protein compounds are selected from the group consisting of immunoglobulins, albumin and a mixture thereof.

21. An apparatus for viral inactivation of a blood product, comprising:
an emitter of type C ultraviolet rays placed so as to emit the type C ultraviolet radiation towards the blood product;
the blood product, wherein the blood product does not contain guenchers, and wherein the blood product is placed in a quartz tube or a tube made of a polymerized material which does not absorb type C ultraviolet radiation; and
a flow meter controlling the flow rate of the blood product such that the blood product retains more than 85% of its activity and is substantially free of nonenveloped viruses.

22. An apparatus according to claim 21, wherein the emitter is a UV lamp, with a power higher than 4 Watt.

23. An apparatus according to claim 21, wherein the type C ultraviolet rays have a wavelength between 250 and 270 nm.

24. An apparatus according to claim 21, wherein the irradiation doses received by the blood product are lower than 640 joules/m$^2$.

25. An apparatus according to claim 21, further comprising a reflecting chamber sending the type C ultraviolet radiation towards the blood product to be treated.

26. An apparatus according to claim 21, further comprising a system for controlling the dose of ultraviolet C radiation which irradiates the blood product to be treated.

27. An apparatus according claim 21, further comprising a system for controlling the temperature of the blood product to be treated.

28. An apparatus according to claim 21, further comprising a pump.

29. An apparatus according to claim 21, wherein the emitter is a UV lamp with a power between 8 and 60 Watts.

30. A method according to claim 21, wherein the type C ultraviolet rays have a wavelength around 254 nm.

31. An apparatus according to claim 21, wherein the irradiation doses received by the blood product are between 10 and 400 joules/m$^2$.

32. An apparatus according to claim 21, wherein the irradiation doses received by the blood product are between 200 and 400 joules/m$^2$.

33. A method for inactivating nonenveloped viruses in a blood product in the apparatus of claim 21, comprising flowing the blood product through the quartz tube or the tube made of a polymerized material which does not absorb type C ultraviolet radiation past the emitter of type C ultraviolet rays, controlling the flow rate of the blood product with the flow meter such that the irradiation doses of ultraviolet radiation which are received by the blood product are lower than 640 joules/m$^2$ and the blood product retains more than 85% of its activity and is substantially free of nonenveloped viruses, wherein the blood product does not contain quenchers when said blood product is subjected to said irradiation doses of ultraviolet radiation.

* * * * *

UNITED STATES PATENT AND TRADEMARK OFFICE
CERTIFICATE OF CORRECTION

PATENT NO.    : 6,190,608 B1
DATED         : February 20, 2001
INVENTOR(S)   : Laub, Ruth, De Wael, Luc, Di Giambattista, Mario Page 1 of 1

It is certified that error appears in the above-identified patent and that said Letters Patent is hereby corrected as shown below:

Column 10,
Line 41, the word "guenchers" should be corrected to reflect the word "quenchers."

Signed and Sealed this

Twelfth Day of March, 2002

*Attest:*

*Attesting Officer*

JAMES E. ROGAN
*Director of the United States Patent and Trademark Office*